(12) United States Patent
Wershofen et al.

(10) Patent No.: US 7,825,276 B2
(45) Date of Patent: Nov. 2, 2010

(54) PROCESS FOR THE PREPARATION OF LIQUID, STORAGE-STABLE ORGANIC ISOCYANATES CONTAINING CARBODIIMIDE AND/OR URETONEIMINE GROUPS

(75) Inventors: Stefan Wershofen, Mönchengladbach (DE); Marcus Steinwegs, Krefeld (DE)

(73) Assignee: Bayer MaterialScience AG, Leverkusen (DE)

( * ) Notice: Subject to any disclaimer, the term of this patent is extended or adjusted under 35 U.S.C. 154(b) by 636 days.

(21) Appl. No.: 11/648,998

(22) Filed: Jan. 3, 2007

(65) Prior Publication Data

US 2007/0155937 A1 Jul. 5, 2007

(30) Foreign Application Priority Data

Jan. 5, 2006 (DE) .................... 10 2006 000 833

(51) Int. Cl.
*C07C 251/00* (2006.01)
(52) U.S. Cl. .................. 560/334; 560/26; 560/115; 560/158; 548/951; 548/952; 548/335.1
(58) Field of Classification Search ............ 560/334, 560/26, 115, 158; 548/951, 952, 335.1; 540/200
See application file for complete search history.

(56) References Cited

U.S. PATENT DOCUMENTS

| 2,853,473 | A | | 9/1958 | Campbell et al. .......... 260/77.5 |
|---|---|---|---|---|
| 4,014,887 | A | | 3/1977 | Randell et al. ......... 260/293.84 |
| 4,085,140 | A | * | 4/1978 | Ibbotson ..................... 564/252 |
| 4,088,665 | A | | 5/1978 | Findeisen et al. .... 260/453 AM |
| 4,340,533 | A | | 7/1982 | Rody ........................ 524/99 |
| 5,202,358 | A | | 4/1993 | Scholl et al. ................. 521/160 |
| 5,218,040 | A | * | 6/1993 | Gras et al. .................... 524/589 |
| 5,354,888 | A | | 10/1994 | Scholl ........................ 564/252 |
| 5,357,021 | A | * | 10/1994 | Tye et al. ..................... 528/28 |
| 6,120,699 | A | | 9/2000 | Narayan et al. ........... 252/182.2 |
| 7,030,274 | B2 | | 4/2006 | Rosthauser et al. ......... 564/252 |
| 2005/0282993 | A1 | | 12/2005 | Rosthauser et al. .......... 528/59 |
| 2006/0025557 | A1 | | 2/2006 | Wershofen et al. |
| 2006/0128928 | A1 | | 6/2006 | Wershofen et al. |
| 2007/0155938 | A1 | | 7/2007 | Wershofen et al. |
| 2007/0155939 | A1 | | 7/2007 | Wershofen et al. |
| 2007/0167633 | A1 | | 7/2007 | Wershofen et al. |

FOREIGN PATENT DOCUMENTS

| DE | 24 01 143 A1 | | 7/1975 |
|---|---|---|---|
| DE | 19622610 | * | 11/1997 |

\* cited by examiner

*Primary Examiner*—Milton I Cano
*Assistant Examiner*—Michael Leonard
(74) *Attorney, Agent, or Firm*—N. Denise Brown; Noland J. Cheung

(57) ABSTRACT

The invention relates to a process for the preparation of liquid, storage-stable isocyanate mixtures of low color number containing carbodiimide (CD) and/or uretonimine (UI) groups, the isocyanate mixtures obtainable by this process and the use thereof for the preparation of blends with further isocyanates and for the preparation of prepolymers containing isocyanate groups and of polyurethane plastics, preferably polyurethane foams.

11 Claims, No Drawings

US 7,825,276 B2

PROCESS FOR THE PREPARATION OF LIQUID, STORAGE-STABLE ORGANIC ISOCYANATES CONTAINING CARBODIIMIDE AND/OR URETONEIMINE GROUPS

CROSS REFERENCE TO RELATED PATENT APPLICATION

The present patent application claims the right of priority under 35 U.S.C. §119 (a)-(d) of German Patent Application No. 10 2006 000 833, filed Jan. 5, 2006.

BACKGROUND OF THE INVENTION

The invention relates to a process for the preparation of liquid, storage-stable isocyanate mixtures of low color number containing carbodiimide (CD) and/or uretonimine (UI) groups, the isocyanate mixtures obtainable by this process, the preparation of blends from these isocyanate mixtures with additional isocyanates, and to a process for the preparation of prepolymers containing isocyanate groups and of polyurethane plastics, and preferably polyurethane foams.

Isocyanate mixtures containing CD and/or UI groups can be prepared in a simple manner using the highly active catalysts from the phospholine series, and particularly the phospholine oxide series of catalysts. Such isocyanate mixtures are prepared by the processes as described in U.S. Pat. Nos. 2,853,473, 6,120,699 and EP-A-515 933.

The high catalytic activity of the phospholine catalysts, and specifically of the phospholine oxide catalysts, on the one hand is desirable in order to start up the carbodiimidization reaction under gentle temperature conditions. However, on the other hand, no process is known to date which ensures effective termination of the phospholine catalysis or phospholine oxide catalysis without limitation. The carbodiimidized isocyanates tend to after-react, i.e. they release gas as a result of evolution of $CO_2$. This then leads to a build up of pressure, for example, in the storage tanks, and especially at higher temperatures.

There has been no lack of attempts to discover an effective means of terminating the phospholine catalysis. Various terminators are mentioned, for example, in the patent specifications DE-A-25 37 685, EP-A-515 933, EP-A-609 698 and U.S. Pat. No. 6,120,699. These terminators include, for example, acids, acid chlorides, chloroformates, silylated acids and halides of the main group elements. The termination of the phospholine catalysts with acids, which, for example, can also be in the form of acid chlorides, is not sufficiently effective.

According to the teaching of EP-A-515 933, CD/UI-containing isocyanate mixtures prepared by means of phospholine catalysis are terminated with at least an equimolar amount, and preferably from 1 to 2 times the molar amount, based on the catalyst employed, of e.g. trimethylsilyl trifluoromethanesulfonate (TMST). In practice, however, it has been found that CD/UI-containing isocyanates prepared in such a way are of only limited suitability for the preparation of prepolymers, i.e. reaction products of these CD/UI-containing isocyanates with polyols. The correspondingly prepared reaction products of polyols and the CD/UI-modified isocyanates tend to release gas, which can lead to a build up of pressure in the transportation tanks or to foaming during the handling of such products.

This problem can be by-passed by employing the silylated acid to terminate the phospholine catalyst analogously to EP-A-515 933 in higher molar equivalents (e.g. 5: 1-10:1, based on the catalyst). In practice, however, it is then found that the resultant CD/UI-modified isocyanates have a significantly poorer color number. This then also applies to the prepolymers prepared therefrom.

This also applies if the phospholine catalyst is terminated with acids of the trifluoromethanesulfonic acid type, in accordance with U.S. Pat. No. 6,120,699. Prepolymers prepared from these CD/UI-modified isocyanates also have a considerably increased color number.

In the preparation of liquid, storage-stable isocyanate mixtures containing carbodiimide (CD) and/or uretonimine (UI) groups, significant variations are sometimes observed in the reactivity of the isocyanate employed, and therefore, in the reaction times required. An undesirable prolonging of the reaction time could be counteracted, for example, by increasing the reaction temperature and/or the catalyst concentration (and as a result the amount of terminator). However, this would be associated with process and/or safety risks and/or quality problems (such as, for example, increased color values).

Thus, the object of the present invention was to provide a simple and economical process for the preparation of liquid, storage-stable and light-colored isocyanate mixtures which contain carbodiimide and/or uretonimine groups that do not have the deficiencies referred to, and leads to liquid, storage-stable isocyanate mixtures of low color numbers.

SUMMARY OF THE INVENTION

The invention relates to a process for the preparation of organic isocyanates containing carbodiimide and/or uretonimine groups. This process comprises partially carbodiimidizing one or more organic isocyanates having a Hazen color number of ≦100 APHA, preferably ≦50 APHA, with one or more catalysts of the phospholine type, and at least one secondary or tertiary amine which contains at least one aliphatic or cycloaliphatic or araliphatic hydrocarbon radical which is optionally substituted and optionally contains heteroatoms; and subsequently terminating the carbodiimidization reaction. By means of this process, the required reaction time can be lowered or kept low and/or the amount of catalyst required can be reduced.

In a specific embodiment of the invention, a sterically hindered, secondary or tertiary amine which contains at least one aliphatic or cycloaliphatic or araliphatic hydrocarbon radical and which is optionally substituted and which optionally contains heteroatoms is employed as the secondary or tertiary amine. In this context, a sterically hindered secondary or tertiary amine is to be understood as meaning a secondary or tertiary amine which carries at least two radicals and/or substituents other than hydrogen on the carbon atoms that are bonded directly to nitrogen atom.

In the process according to the invention, one secondary or tertiary amine which contains at least one aliphatic or cycloaliphatic or araliphatic hydrocarbon radical and which is optionally substituted and which optionally contains heteroatoms, or also a mixture of several different such secondary or tertiary amines can be used. In this context, the secondary or tertiary amine which contains at least one aliphatic or cycloaliphatic or araliphatic hydrocarbon radical which is optionally substituted and which optionally contains heteroatoms can be added directly to the starting isocyanate or to the reaction mixture during the carbodiimidization reaction. The secondary or tertiary amine which contains at least one aliphatic or cycloaliphatic or araliphatic hydrocarbon radical which is optionally substituted and which optionally contains heteroatoms is preferably added here in substance, i.e. without dilution, or as a masterbatch. A suitable masterbatch is, for example, present as a solution of the secondary or tertiary amine which contains at least one aliphatic or cycloaliphatic or araliphatic hydrocarbon radical which is optionally substituted and which optionally contains heteroatoms in the starting isocyanate or in previously carbodiimidized isocyanate or as a solution in a suitable solvent.

The present invention also relates to the organic isocyanates containing carbodiimide and/or uretonimine groups which are obtainable by the abovementioned process. These organic isocyanates containing carbodiimide and/or uretonimine groups are liquid at room temperature, and, depending on the CD/UI content and/or on the isocyanate employed, may be liquid down to low temperatures (e.g. 0° C.).

The present invention also provides a process for the preparation of isocyanate blends. These blends comprise the organic isocyanates containing carbodiimide and/or uretonimine groups according to the invention, and at least one other isocyanate component which is different than the isocyanates of the invention which contain carbodiimide and/or uretonimine groups. This invention also provides a process for the preparation of prepolymers which contain isocyanate groups and exhibit an improved color number from the isocyanates containing CD and/or UI groups of this invention.

Finally, the invention also provides a process for the preparation of polyurethane plastics, and preferably polyurethane foams, comprising reacting the organic isocyanates containing carbodiimide and/or uretonimine groups of the invention with at least one isocyanate-reactive component.

DETAILED DESCRIPTION OF THE INVENTION

As described and used herein, the Hazen color number can be measured in accordance with DIN/EN/ISO 6271-2 (draft of September 2002) in substance against water as the reference, at a layer thickness of 5 cm. For the measuring instrument, a Dr. Lange LICO 300 photometer e.g. can be employed.

Organic isocyanates having a higher color number can, of course, also be used as starting substances. When these higher color number isocyanates are used, however, the advantages with respect to the favorable color values are not utilized to the full extent.

Suitable organic isocyanates to be used as starting materials for the present invention include any desired organic isocyanates which have a Hazen color number of ≦100 APHA, preferably ≦50 APHA. It is preferred that the process according to the invention provides for the carbodiimidization of organic diisocyanates which can in turn be employed in polyurethane chemistry.

Organic isocyanates having a higher color number can, of course, also be used as starting substances. In this case, however, the advantages with respect to the favorable color values cannot be utilized to the full extent.

Suitable isocyanates to be used in accordance with the present invention include, for example, aromatic, araliphatic, aliphatic and/or cycloaliphatic diisocyanates and/or polyisocyanates.

Representatives of the aliphatic and/or cycloaliphatic diisocyanates which may be mentioned by way of example are isophorone-diisocyanate, hexamethylene-diisocyanate and dicyclohexylmethane-diisocyanate. In each case, the pure isomers and/or any desired isomer mixtures may be used herein.

Representatives of the araliphatic diisocyanates which may be mentioned by way of example are the various isomers of xylidene-diisocyanates.

Aromatic di-and polyisocyanates, such as toluene-diisocyanate, and di-and polyisocyanates of the diphenylmethane series, are suitable for the starting isocyanate component of the present invention.

In particular, the following isocyanates are suitable starting materials:

aromatic diisocyanates, such as 2,4-and/or 2,6-diisocyanatotoluene (TDI), 2,2'-, 2,4'-and/or 4,4'-diisocyanatodiphenylmethane (MDI) and any desired mixtures of such aromatic diisocyanates;

and di-and polyisocyanate mixtures of the diphenylmethane series having a content of monomeric diisocyanatodiphenylmethane isomers of from 80 to 100 wt. % and a content of polyisocyanates of the diphenylmethane series which are more than difunctional of from 0 to 20 wt. %, with the diisocyanatodiphenylmethane isomers being composed of 0 to 100% by weight of 4,4'-diisocyanatodiphenylmethane, 100 to 0% by weight of 2,4'-diisocyanatodiphenylmethane, and 0 to 8% by weight of 2,2'-diisocyanatodiphenylmethane, with the sum of the percentages of the three isomers totalling 100% by weight of the monomer.

Organic isocyanates which are preferred as starting materials are, in particular, aromatic diisocyanates, such as 2,4-and/or 2,6-diisocyanatotoluene (TDI), 2,2'-, 2,4'-and/or 4,4'-diisocyanatodiphenylmethane (MDI) and any desired mixtures of such aromatic diisocyanates. More preferred starting materials are 2,2'-, 2,4'-and/or 4,4'-diisocyanatodiphenylmethane (MDI) and any desired mixtures of such aromatic diisocyanates, with the sum of 2,2'-, 2,4'-and/or 4,4'-diisocyanatodiphenylmethane in the starting material (organic isocyanate) being at least 85% by weight of the total weight, and the diisocyanatodiphenylmethane isomers being composed of from 0 to 100% by weight of 4,4'-diisocyanatodiphenylmethane, from 100 to 0% by weight of 2,4'-diisocyanatodiphenylmethane and of from 0 to 8% by weight of 2,2'-diisocyanatodiphenylmethane, with the sum of the percentages stated totalling 100% by weight. Most preferred starting materials are 2,2'-, 2,4'-and/or 4,4'-diisocyanatodiphenylmethane (MDI), and any desired mixtures of aromatic diisocyanates, with the sum of 2,2'-, 2,4'-and/or 4,4'-diisocyanatodiphenylmethane in the starting material (i.e. the starting organic isocyanate) being at least 90% by weight, and the diisocyanatodiphenylmethane isomers being composed of 0 to 100% by weight of 4,4'-diisocyanatodiphenylmethane, 100 to 0% by weight of 2,4'-diisocyanatodiphenylmethane and 0 to 8% by weight of 2,2'-diisocyanatodiphenylmethane, with the sum of the percentages of the three isomers totalling 100% by weight. Most particularly preferred starting materials are 2,2'-, 2,4'-and/or 4,4'-diisocyanatodiphenylmethane (MDI) and any desired mixtures of aromatic diisocyanates, with the sum of 2,2'-, 2,4'-and/or 4,4'-diisocyanatodiphenylmethane present in the starting material (i.e. the starting organic isocyanate) being at least 99% by weight and the diisocyanatodiphenylmethane isomers being composed of 0 to 100% by weight of 4,4'-diisocyanatodiphenylmethane, 100 to 0% by weight of 2,4'-diisocyanatodiphenylmethane, and 0 to 8% by weight of 2,2'-diisocyanatodiphenylmethane, with the sum of the percentages stated for the three isomers totalling 100% by weight.

The process according to the invention is carried out in the presence of catalysts of the phospholine type. The catalysts of the phospholine type are known and described in, for example, EP-A-515 933 and U.S. Pat. No. 6,120,699, the disclosures of which are hereby incorporated by reference.

Typical examples of these catalysts are, for example, the mixtures, known from the prior art, of the phospholine oxides which correspond to the formulas:

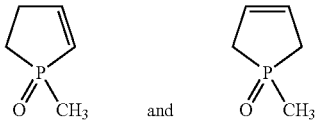 and

The amount of catalyst employed depends on the quality and/or the reactivity of the starting isocyanates. Thus, the specific amount of catalyst needed can most easily and readily be determined in a preliminary experiment.

By using at least one secondary or tertiary amine which contains at least one aliphatic or cycloaliphatic or araliphatic hydrocarbon radical which is optionally substituted and which optionally contains heteroatoms, the reactivity of the starting isocyanate is increased. This can occur, for example, because these secondary or tertiary amines counteract the reactivity-reducing action of secondary components in the starting isocyanate which potentially split off HCl (i.e hydrochloric acid), in that they act as bases and bond HCl as hydrochloride. Other action mechanisms are, however, also possible.

Suitable secondary or tertiary amine to be used in accordance with the present invention include, for example, those secondary or tertiary amines which contain at least one aliphatic or cycloaliphatic or araliphatic hydrocarbon radical which is optionally substituted and which optionally contains heteroatoms. In a particular embodiment, these include the sterically hindered secondary or tertiary amines which, for example, are amines corresponding to the general structure (I), and cyclic amines, such as the amines corresponding to the general structure (II) which are derived from pyrrolidine, or the cyclic amines corresponding to the general structure (III) which are derived from piperidine:

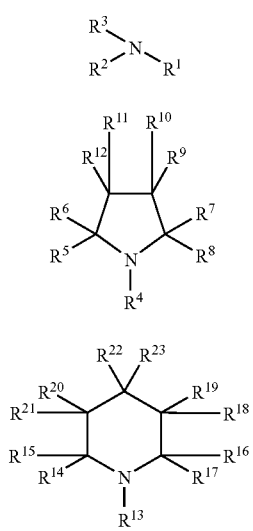

Suitable amines include those which correspond to the general structure (I),

wherein:
R$^1$, R$^2$ and/or R$^3$ each independently of one another represents a hydrogen atom, or an aliphatic, cycloaliphatic, aromatic or araliphatic radical which optionally contains heteroatoms and/or which optionally contains additional functional groups, such as, for example, hydroxyl groups and/or amino groups, with the proviso that only one of R$^1$, R$^2$ and/or R$^3$ may represent hydrogen at one time.

In the general structure (I) for the secondary or tertiary amines, R$^1$, R$^2$ and R$^3$ can be either all identical or all different, or two of the radicals R$^1$, R$^2$ and R$^3$ can be identical. Likewise, it is possible for two or three of the radicals R$^1$, R$^2$ and R$^3$ to be bonded to one another and thus form cyclic or bicyclic structures in structure (I). In addition, at least one of the radicals R$^1$ to R$^3$ of structure (I) is preferably selected from the group consisting of aliphatic, cycloaliphatic or araliphatic hydrocarbon radicals which can contain heteroatoms and/or additional functional groups (substituents), such as e.g. hydroxyl groups and/or amino groups.

Suitable amines which correspond to the general structure (II) are those which are derived from pyrrolidine. Suitable amines those corresponding to general structure (II)

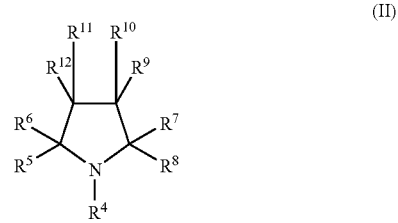

wherein:
R$^4$ represents a hydrogen atom, or an aliphatic, cycloaliphatic, aromatic or araliphatic radical which can optionally contain heteroatoms and/or can optionally contain additional functional groups, such as e.g. hydroxyl groups and/or amino groups;
and
R$^5$ to R$^{12}$ each independently of one another represent a hydroxyl group, an amino group, or an aliphatic, cycloaliphatic, aromatic or araliphatic radical which can optionally contain heteroatoms and/or can optionally contain additional functional groups, such as e.g. hydroxyl groups and/or amino groups.

In general structure (II), the radicals R$^5$ to R$^{12}$ can be either all identical or all different, or two or more of the radicals R$^5$ to R$^{12}$ can in each case be identical. Likewise, it is possible for two or more of the radicals R$^5$ to R$^{12}$ to be bonded to one another and to thus form cyclic, bicyclic or polycyclic (part) structures. In addition, at least one of the radicals R$^4$ to R$^{12}$ of structure (II) is selected from the group consisting of aliphatic, cycloaliphatic or araliphatic hydrocarbon radicals which can contain heteroatoms and/or additional functional groups (substituents), such as e.g. hydroxyl groups and/or amino groups.

Suitable amines which correspond to the general structure (III) are those which are derived from piperidine. These amines may correspond to general structure (III)

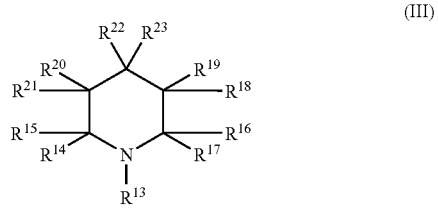

wherein:
$R^{13}$ represents a hydrogen atom, or an aliphatic, cycloaliphatic, aromatic or araliphatic radical which can optionally contain heteroatoms and/or which can optionally contain additional functional groups, such as e.g. hydroxyl groups and/or amino groups; and
$R^{14}$ to $R^{23}$ each independently of one another represents a hydroxyl group, an amino group, or an aliphatic, cycloaliphatic, aromatic or araliphatic radical which can optionally contain heteroatoms and/or which can optionally contain additional functional groups, such as e.g. hydroxyl groups and/or amino groups.

In structure (III), the radicals $R^{14}$ to $R^{23}$ can be either all identical or all different, or two or more of the radicals $R^{14}$ to $R^{23}$ can in each case be identical. Likewise, it is possible for two or more of the radicals $R^{14}$ to $R^{23}$ to be bonded to one another and to thus form cyclic, bicyclic or polycyclic (part) structures. In addition, at least one of the radicals $R^{13}$ to $R^{23}$ of structure (III) is selected from the group consisting of aliphatic, cycloaliphatic or araliphatic hydrocarbon radicals which can optionally contain heteroatoms and/or which can optionally contain additional functional groups (substituents), such as e.g. hydroxyl groups and/or amino groups.

Examples of the aliphatic radicals include, for example, methyl, ethyl, propyl, isopropyl, n-butyl, isobutyl, sec-butyl, tert-butyl and higher, optionally branched n-, iso-, sec-or tert-alkyl groups. It is also possible for the aliphatic radicals to contain heteroatoms and/or to carry further functional groups, such as e.g. hydroxyl groups and/or amino groups.

Examples of the cycloaliphatic radicals include, for example, cyclopropyl, cyclobutyl, cyclopentyl, cyclohexyl and higher, optionally branched cycloalkyl groups. It is also possible for the cycloaliphatic radicals to contain heteroatoms and/or to carry further functional groups, such as e.g. hydroxyl groups and/or amino groups.

Examples of the aromatic radicals include, for example, phenyl, tolyl, ethylphenyl, other mono-or polysubstituted phenyl groups, naphthyl, other mono-or polysubstituted naphthyl groups and other unsubstituted or mono-or polysubstituted and/or optionally fused aromatic radicals. It is also possible for the aromatic radicals to contain heteroatoms and/or to carry further functional groups, such as e.g. hydroxyl groups and/or amino groups.

Examples of the araliphatic radicals include, for example, benzyl, mono-or polysubstituted benzyl groups, 1-phenylethyl, mono-or polysubstituted 1-phenylethyl groups, 2-phenylethyl, mono-or polysubstituted 2-phenylethyl groups and other unsubstituted or mono-or polysubstituted and/or optionally fused araliphatic radicals. It is also possible for the araliphatic radicals to contain heteroatoms and/or to carry further functional groups, such as e.g. hydroxyl groups and/or amino groups.

Suitable secondary or tertiary amines which contains at least one aliphatic or cycloaliphatic or araliphatic hydrocarbon radical which is optionally substituted and optionally contains heteroatoms include compounds such as, for example, Sanol® LS 2626 {4-[3-(3,5-di-tert-butyl-4-hydroxyphenyl)propionyloxy]-1-[2-[3-(3,5-di-tert-butyl-4-hydroxyphenyl)-propionyloxy]ethyl]-2,2,6,6-tetramethylpiperidine}, which is also known as a color stabilizer, and alkylpiperidines, such as, for example, 1,2,2,6,6-pentamethyl-4-piperidinol or 2,2,6,6-tetramethyl-4-piperidinol.

The compounds mentioned specifically are regarded only as examples. The suitable secondary or tertiary amine which contain at least one aliphatic or cycloaliphatic or araliphatic hydrocarbon radical which is optionally substituted and optionally contains heteroatoms are not limited to the specific compounds mentioned herein.

The secondary or tertiary amine which contains at least one aliphatic or cycloaliphatic or araliphatic hydrocarbon radical which is optionally substituted and optionally contains heteroatoms, or the mixture of several different secondary or tertiary amines which contain at least one aliphatic or cycloaliphatic or araliphatic hydrocarbon radical which is optionally substituted and optionally contains heteroatoms can be added in several different ways. For example, these secondary or tertiary amines can be added immediately before, at the same time as or also, only after the addition of the catalyst to the starting isocyanate. It is preferred that the secondary or tertiary amine which contains at least one aliphatic or cycloaliphatic or araliphatic hydrocarbon radical which is optionally substituted and optionally contains heteroatoms is added to the starting isocyanate before the addition of the catalyst. In another preferred embodiment, the secondary or tertiary amine which contains at least one aliphatic or cycloaliphatic or araliphatic hydrocarbon radical which is optionally substituted and optionally contains heteroatoms is added only after the addition of the catalyst, i.e. during the carbodiimidization reaction. The best point in time for the addition can also be determined in a simple preliminary experiment, and is preferably before reaching 90%, and more preferably before reaching 70% of the total desired conversion of isocyanate.

The optimum amount of the secondary or tertiary amine which contains at least one aliphatic or cycloaliphatic or araliphatic hydrocarbon radical which is optionally substituted and optionally contains heteroatoms which is employed can likewise be determined in a simple preliminary experiment. It is preferred to use $\leq 1,000$ ppm, more preferred to use $\leq 250$ ppm and most preferred to use $\leq 100$ ppm of the secondary or tertiary amine, based on the total weight of the starting isocyanate employed.

The secondary or tertiary amine which contains at least one aliphatic or cycloaliphatic or araliphatic hydrocarbon radical which is optionally substituted and optionally contains heteroatoms can thus be added directly to the starting isocyanate, or to the reaction mixture during the carbodiimidization reaction. In this context, the secondary or tertiary amine which contains at least one aliphatic or cycloaliphatic or araliphatic hydrocarbon radical which is optionally substituted and optionally contains heteroatoms is preferably added in substance, i.e. without dilution, or as a masterbatch. A masterbatch, for example, is present as a solution of the secondary or tertiary amine which contains at least one aliphatic or cycloaliphatic or araliphatic hydrocarbon radical which is optionally substituted and optionally contains heteroatoms in the starting isocyanate or in already carbodiimidized isocyanate or as a solution in a suitable solvent.

The addition of the secondary or tertiary amine which contains at least one aliphatic or cycloaliphatic or araliphatic hydrocarbon radical which is optionally substituted and optionally contains heteroatoms results in a higher reactivity with respect to the carbodiimidization reaction. As a result of this hither reactivity, either the reaction time required and/or the amount of catalyst required can be reduced.

The carbodiimidization reaction is conventionally carried out in the temperature range between 50 to 150° C., preferably from 60 to 100° C. However, significantly higher reaction temperatures are also possible (i.e. up to approx. 280° C.). The optimum reaction temperature for the carbodiimidization reaction depends on the nature of the starting isocyanates and/or of the catalyst employed, and can be determined in a simple preliminary experiment.

The carbodiimidization reaction is, in general, interrupted when a degree of carbodiimidization of from 3 to 50%, and preferably from 5 to 30%, is reached. The phrase "the degree of carbodiimidization" refers to the percentage of carbodiimidized isocyanate groups, with respect to the total amount of isocyanate groups present in the starting isocyanate.

The degree of carbodiimidization can be determined while the process according to the invention is being carried out, by determination of the % NCO by, for example, means of titration, which is known per se to the person skilled in the art, or by means of suitable online methods. A suitable online method is, for example, near infra-red or middle infra-red analysis.

The degree of carbodiimidization can likewise be ascertained while the process according to the invention is being carried out, for example, from the amount (i.e. quantity) of carbon dioxide escaping in the reactor mixture. This amount of carbon dioxide, which can be determined volumetrically, thus provides information about the degree of carbodiimidization reached at any point in time.

Furthermore, in principle, other suitable offline or online methods of process monitoring which are known to the person skilled in the art can also be employed.

To end the carbodiimidization reaction, it is preferable to add at least the equimolar amount, more preferably a 1-to 20-fold molar excess, and most preferably a 1-to 10-fold molar excess, based on the weight of the catalyst, of a terminator or an alkylating agent. A mixture of terminators may also be employed.

A preferred catalyst terminator is trimethylsilyl trifluoromethanesulfonate (TMST). In this context, an alkylating agent or trimethylsilyl trifluoromethanesulfonate (TMST) is preferably employed as the sole terminator.

Preferred alkylating agents are esters of trifluoromethanesulfonic acid, esters of inorganic acids (preferably strong inorganic acids) or trialkyloxonium compounds.

The reaction product of the carbodiimidization reaction can contain color stabilizers such as those which are conventionally added to isocyanates. In this context, the point in time of the addition of the stabilizers is not critical. The color stabilizers can be added either to the isocyanate which is used as the starting material, before the carbodiimidization, or to the reaction product when the carbodiimization reaction has ended. Likewise, it is possible to add color stabilizers to both the starting material and to the reaction product. Such stabilizers are generally known to the person skilled in the art and include e.g. substances from the group consisting of sterically hindered phenols, phosphorous acid esters or sterically hindered amines. The color stabilizers can in each case be employed by themselves or in a mixture with other representatives of the same or different substance groups. The amounts of color stabilizers employed varies in the order of magnitude known to the person skilled in the art, conventionally in the range of from 100 ppm to 10,000 ppm for the individual substance or the mixture, based on the total weight of the isocyanate used as the starting material or of the reaction product of the carbodiimidization.

Prepolymers containing isocyanate groups are obtained by, for example, reaction of the organic isocyanates containing carbodiimide and/or uretonimine groups which are prepared by the process of the present invention with one or more conventional polyols which are known to be suitable in polyurethane chemistry. Suitable polyols include both simple polybasic alcohols having a molecular weight in the range of from 62 to 599 g/mol, preferably 62 to 300 g/mol, such as e.g. ethylene glycol, trimethylolpropane, propane-1,2-diol, butane-1,2-diol or butane-2,3-diol, hexanediol, octanediol, dodecanediol and/or octadecanediol, and in particular, higher molecular weight polyether polyols and/or polyester polyols of the type known per se from polyurethane chemistry which have molecular weights of from 600 to 8,000 g/mol, preferably 800 to 4,000 g/mol. Such higher molecular weight compounds typically contain at least two, and as a rule from 2 to 8, and preferably from 2 to 4 primary and/or secondary hydroxyl groups. Examples of such polyols are described in, for example, U.S. Pat. No. 4,218,543, at column 7, line 29 to column 9, line 32, the disclosure of which is hereby incorporated by reference.

The advantages of the process according to the invention are apparent: The reactivity of the reaction mixture is increased and/or standardized by the presence of a secondary or tertiary amine during the carbodiimidization. As a result, the required reaction time can be lowered or kept low and/or the required amount of catalyst can be reduced. Both the isocyanates containing carbodiimide and/or uretonimine groups and the prepolymers prepared therefrom furthermore have a good storage stability and a light color.

These organic isocyanates containing carbodiimide and/or uretonimine groups and the prepolymers prepared therefrom by reaction of the isocyanates of the invention with polyols are valuable starting materials for the preparation of polyurethane plastics by the reaction of the isocyanates of the invention or prepolymers thereof with one or more polyols (e.g. polyether polyols and/or polyester polyols) by the isocyanate polyaddition process.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

The following starting substances were used in the working examples:

Isocyanate A: 4,4'-diphenylmethane diisocyanate having an NCO group content of 33.6% by weight (Desmodur 44M®, Bayer AG)

Catalyst A: a technical-grade mixture of 1-methyl-1-oxo-1-phosphacyclopent-2-ene and 1-methyl-1-oxo-1-phosphacyclopent-3-ene, 1 wt. % strength in toluene Terminator A: trifluoromethanesulfonic acid ethyl ester (TFMSEE)

Amine A: 4-[3-(3,5-di-tert-butyl-4-hydroxyphenyl)propionyloxy]-1-[2-[3-(3,5-di-tert-butyl-4-hydroxyphenyl)-propionyloxy]ethyl]-2,2,6,6-tetramethylpiperidine; commercially available as Sanol® LS 2626

Amine B: 1,2,2,6,6-pentamethyl-4-piperidinol

Amine C: 2,2,6,6-tetramethyl-4-piperidinol

Amine D: triphenylamine

The following general instructions were used for the preparation of the organic isocyanate containing carbodiimide and/or uretonimine groups:

10 kg of Isocyanate A having a Hazen color number of ≦15 APHA, which contained 750 ppm 3,5-di-tert-butyl-4-hydroxytoluene, were heated to approx. 90° C. under $N_2$/while stirring. The amount of catalyst solution as shown in the table in order to achieve the desired amount of catalyst was then added. The corresponding amount of the secondary or tertiary amine was added to the reaction mixture (see the table for details including which secondary or tertiary amine was added, the specific point in time of the addition, and the amount of secondary or tertiary amine added in each example). The reaction mixture was heated at approx. 95° C. under $N_2$/while stirring until the desired NCO content was reached. Thereafter, the carbodiimidization reaction was terminated by the addition of the specific terminator (i.e. trifluoromethanesulfonic acid ethyl ester (TFMSEE)); see table for specific details) and the mixture was subsequently stirred for 1 hour.

Amines A, B and C belong to the group of amines required by the present invention. Each of these three amines is a secondary or tertiary amine which contains at least one aliphatic or cycloaliphatic or araliphatic hydrocarbon radical, which is optionally substituted and optionally contains heteroatoms. Amine D is a comparative amine which contains exclusively aromatic hydrocarbon radicals.

The results are summarized in the following table.

The Hazen color number was measured in accordance with DIN/EN/ISO 6271-2 (draft of September 2002), in substance against water as the reference at a layer thickness of 5 cm. A Dr. Lange LICO 300 photometer was employed as the measuring instrument.

A comparison of Example 1 which is representative of the invention and Comparison Example 1 illustrates that, in spite of the same catalyst concentration and approximately the same concentration of hydrolysable chlorine, the addition of the secondary or tertiary amine which contains at least one aliphatic or cycloaliphatic or araliphatic hydrocarbon radical which is optionally substituted and optionally contains heteroatoms as in Example 1, resulted in a shortened reaction time. This even applied when the concentration of catalyst in the examples according to the invention was reduced. A comparison of Example 1 (representative of the present invention) and Comparison Example 2 illustrates the shortening of the reaction time by the addition of a secondary or tertiary amine which contains at least one aliphatic or cycloaliphatic or araliphatic hydrocarbon radical which is optionally substituted and optionally contains heteroatoms, was much greater than that which resulted from the addition of a tertiary amine substituted exclusively by aromatic hydrocarbon radicals as in Comparison Example 2.

The products obtained in the examples according to the invention also achieved a very good color level (HAZEN) which was improved significantly compared with Comparison Example 1.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of organic isocyanates containing carbodiimide and/or uretonimine groups, comprising
A) partially carbodiimidizing
(1) one or more organic isocyanates having a Hazen color number of ≦100 APHA,
in the presence of
(2) one or more catalysts of the phospholine type, and
(3) at least one secondary amine which contains at least one aliphatic or cycloaliphatic or araliphatic hydrocarbon radical which is optionally substituted and which optionally contains heteroatoms,
wherein (3) said secondary amine is present in concentrations of ≦1,000 ppm, based on the weight of the isocyanate employed, and said secondary amine corresponds to a general structure selected from the group consisting of:

| | Educt Reaction conditions | | | | | | | | |
|---|---|---|---|---|---|---|---|---|---|
| | | Catalyst | Terminator | | Concentration | | | Product | Viscosity |
| | Hydrolysable chlorine [ppm] | concentration [ppm] | Terminator | concentration [ppm] | Amine | of the amine [ppm] | Reaction time [min] | NCO value [%] | HAZEN [APHA] | at 25° C. [mPas] |
| Comparison Example 1 | 16 | 2.5 | TFMSEE | 50 | — | — | 380 | 29.6 | 217 | 28 |
| Comparison Example 2 | 14 | 2.5 | TFMSEE | 50 | D | 100 | 315 | 31.1 | — | — |
| Example 1 | 14 | 2.5 | TFMSEE | 50 | A | 250 | 240 | 29.6 | 46 | 32 |
| Example 2 | 10 | 0.5 | TFMSEE | 40 | B | 50 | 220 | 29.6 | 35 | 29 |
| Example 3 | 11 | 0.5 | TFMSEE | 40 | C | 50 | 250 | 29.9 | 26 | 26 | structure (II):

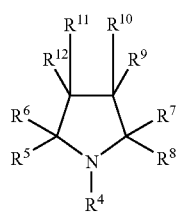

wherein:
R⁴ represents a hydrogen atom; and
R⁵ to R¹² each independently represents a hydroxyl group, an amino group, or aliphatic, cycloaliphatic, aromatic or araliphatic hydrocarbon radical which can optionally contain heteroatoms and which can optionally carry additional functional groups, and in which two or more of the radicals R⁵ to R¹² can be bonded to one another to form cyclic, bicyclic or polycyclic structures;
with the proviso that (i) at least one of the radicals R⁵ to R¹² is selected from the group consisting of aliphatic, cycloaliphatic or araliphatic hydrocarbon radicals which are optionally substituted and which optionally contain heteroatoms:

and
structure (III):

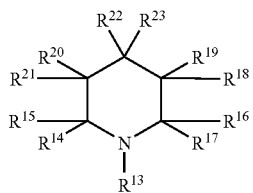

wherein:
R¹³ represents a hydrogen atom;
R¹⁴ to R¹⁷ each independently represents an aliphatic hydrocarbon radical which can optionally contain heteroatoms and which can optionally carry additional functional groups, and in which two or more of the radicals R¹⁴ to R¹⁷ can be bonded to one another to form cyclic, bicyclic or polycyclic structures;
and
R¹⁸ to R²³: each independently represents a hydrogen atom, a hydroxyl group, an amino group, or an aliphatic, cycloaliphatic, aromatic or araliphatic hydrocarbon radical which can optionally contain heteroatoms and which can optionally carry additional functional groups, and in which two or more of the radicals R¹⁸ to R²³ can be bonded to one another to form cyclic, bicyclic or polycyclic structures;

and subsequently,
(B) terminating the carbodiimidization.

2. The process of claim 1, wherein (3) said secondary amine is 2,2,6,6-tetramethyl-4-piperidinol.

3. The process of claim 1, where in (1) said one or more organic isocyanates has a Hazen color number of ≦50 APHA.

4. The process of claim 1 wherein (3) said secondary amine is added immediately before, at the same time as or after the addition of (2) the catalyst.

5. The process of claim 1, wherein (3) said secondary amine is present in concentrations of ≦250 ppm, based on the weight of the isocyanate employed.

6. The process of claim 1, wherein (3) said secondary or tertiary amine is present in concentrations of ≦100 ppm, based on the weight of the isocyanate employed.

7. The process of claim 4, wherein (3) said secondary amine is added in substance.

8. The process of claim 4, wherein (3) said secondary amine is added as a masterbatch in the starting isocyanate or in previously carbodiimidized isocyanate or in a suitable solvent.

9. Organic isocyanates containing carbodiimide and/or uretonimine groups produced by the process of claim 1.

10. A process for the preparation of isocyanate blends comprising blending one or more organic isocyanates containing carbodiimide and/or uretonimine groups of claim 9, with a second isocyanate component.

11. A process for the preparation of isocyanate prepolymers or polyurethanes comprising reacting one or more of the organic isocyanates containing carbodiimide and/or uretonimine groups of claim 9 with one or more compounds containing isocyanate-reactive groups.

* * * * *